United States Patent [19]

Hagen et al.

[11] Patent Number: 5,270,685
[45] Date of Patent: Dec. 14, 1993

[54] SYRINGE PRESSURE MONITOR

[75] Inventors: Ronald W. Hagen, St. Charles; Duane L. Horton, St. Louis, both of Mo.

[73] Assignee: Mallinckrodt Medical, Inc., St. Louis, Mo.

[21] Appl. No.: 724,669

[22] Filed: Jul. 2, 1991

[51] Int. Cl.$^5$ ............................................. G08B 21/00
[52] U.S. Cl. ................................... 340/626; 340/603; 128/DIG. 12; 128/DIG. 13; 604/121
[58] Field of Search ............... 340/626, 611, 614, 603, 340/606; 200/85 R, 5 A; 128/DIG. 12, DIG. 13; 73/380; 604/118, 121

[56] References Cited

U.S. PATENT DOCUMENTS

| | | | |
|---|---|---|---|
| 3,771,694 | 11/1973 | Kaminski | 128/DIG. 13 |
| 4,370,982 | 2/1983 | Reilly | 604/98 |
| 4,547,635 | 10/1985 | Segan et al. | 200/85 R X |
| 4,759,750 | 7/1988 | DeVries | 604/121 |

Primary Examiner—Jin F. Ng
Assistant Examiner—Jeffery A. Hofsass
Attorney, Agent, or Firm—Rita Downard Vacca

[57] ABSTRACT

A pressure monitoring device for indicating to the administrator of an injection to a patient that an excess of force has been exerted on the plunger and thereby the fluids contained within the syringe.

3 Claims, 2 Drawing Sheets

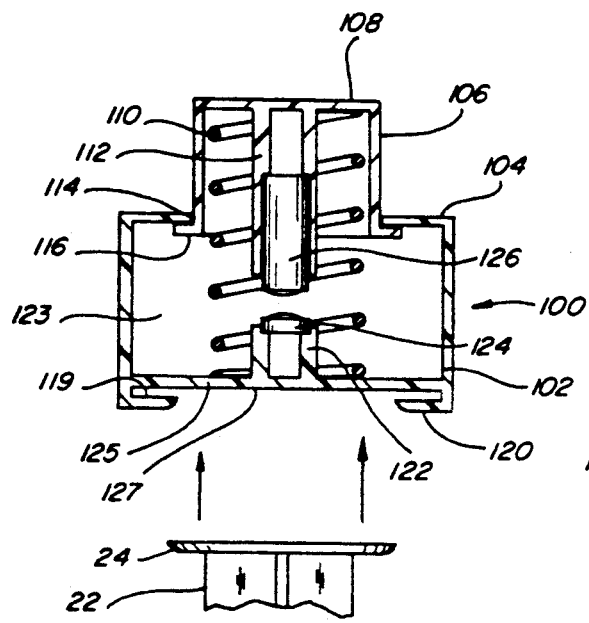
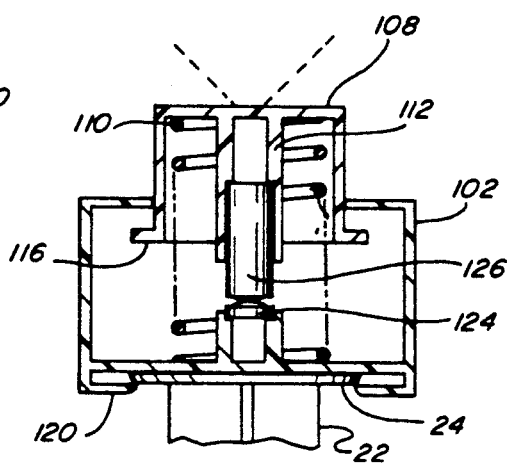
Fig. 6
Fig. 7
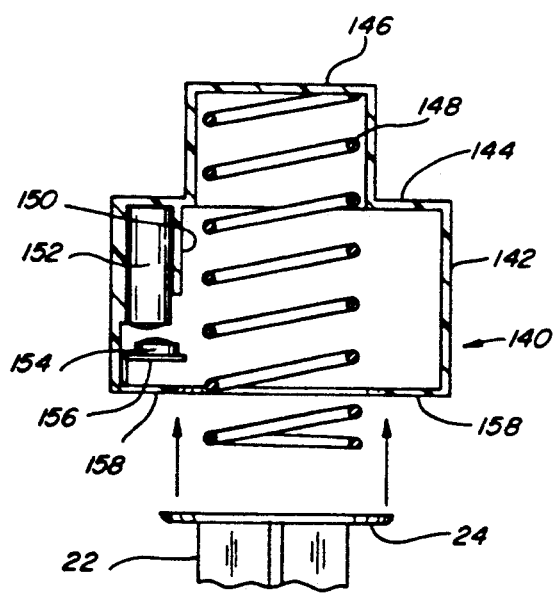
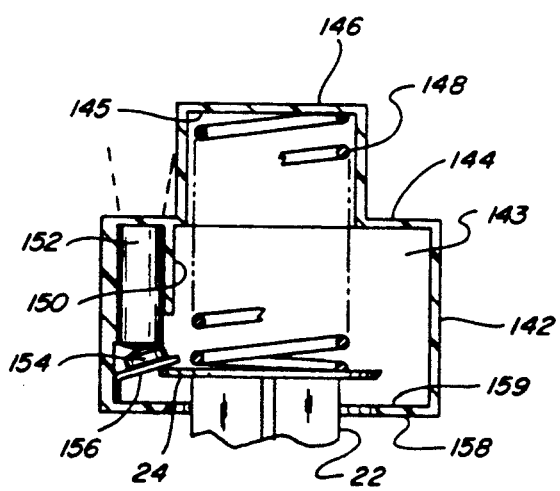
Fig. 8
Fig. 9

SYRINGE PRESSURE MONITOR

BACKGROUND OF THE INVENTION

This invention relates to a syringe pressure monitor and, more particularly, to a reusable multiportioned pressure monitoring device for attachment to a plunger portion of a syringe.

During the intravenous administration of various pharmaceutical agents, a means of monitoring the force applied to a syringe plunger or piston and therefore the pressure generated on the fluids within the syringe is often necessary. Although various devices which allow for dose and delivery time measurement have heretofore been provided, none have been particularly adapted for monitoring the pressure exerted on the contents contained within a syringe. Monitoring the pressure exerted on the contents of a syringe is especially useful and necessary when injecting pharmaceuticals containing microbubbles which burst under excessive pressure. There is, therefore, a need for the present syringe pressure monitoring device which particularly lends itself to intravenous administration of a pharmaceutical agent to a patient while allowing for the monitoring of the pressure exerted thereon by means of the syringe plunger.

In general, it is an object of the present invention to provide a reusable syringe pressure monitoring device to provide a means of monitoring the pressure exerted on a fluid or fluids within a syringe.

Another object of the invention is to provide a syringe pressure monitoring device of the above character which is easy and convenient to use.

Another object of the present invention is to provide a syringe pressure monitoring device of the above character which is inexpensive and can be easily constructed.

Additional objects and features of the present invention will appear from the following description in which the preferred embodiments are set forth in detail in conjunction with the accompanying drawings.

FIG. 6 is a cross-sectional view of another embodiment of the syringe pressure monitoring device of FIG. 1 attached to a plunger portion of a syringe;

FIG. 7 is a cross-sectional view of the syringe pressure monitoring device of FIG. 6 attached to a plunger portion of a syringe and compressed;

FIG. 8 is cross-sectional view of still another embodiment of the syringe pressure monitoring device of FIG. 1 attached to a plunger portion of a syringe; and FIG. 9 is a cross-sectional view of the syringe pressure monitoring device of FIG. 8 attached to a plunger portion of a syringe and compressed.

SUMMARY OF THE INVENTION

A pressure monitoring device of the present invention is employed to monitor the pressure exerted on the fluid(s) contents of a syringe during the administration thereof to a patient. Often times it is important to monitor the pressure exerted on the fluids within a syringe for the purpose of measuring the dose and delivery time to the patient. However, the need for a pressure monitoring device of the present invention is now of even greater importance due to the current use of pharmaceuticals containing microbubbles for diagnostic imaging. If an excess of force is used in injecting such pharmaceuticals, the microbubbles contained therein are crushed under the pressure exerted thereon and images created therefrom are inferior to non-existent in comparison to such pharmaceuticals not subject to high pressures. Therefore, the present pressure monitoring device comprising a shell portion, a spring within the shell portion and an indicator means within said shell portion is designed whereby upon compression of the spring within the shell portion initiates a signal from the indicator means indicating to the administrator of the injection that too much force has been used.

DETAILED DESCRIPTION OF THE INVENTION

Figure 1:
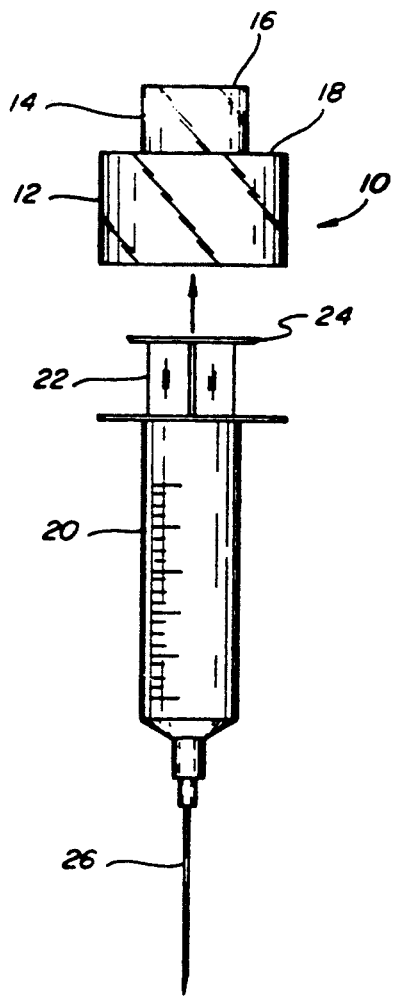
FIG. 1 is a side view of a syringe pressure monitoring device of the present invention and a syringe.
Figure 2:
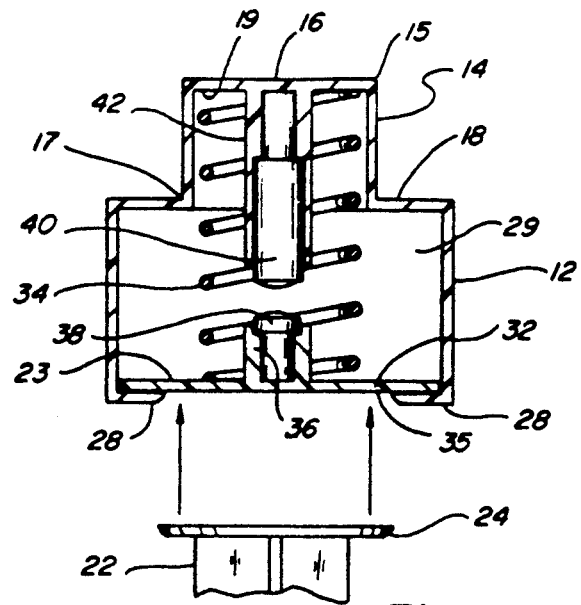
FIG. 2 is a cross-sectional view of the syringe pressure monitoring device of FIG. 1 attached to a plunger portion of a syringe.
Figure 3:
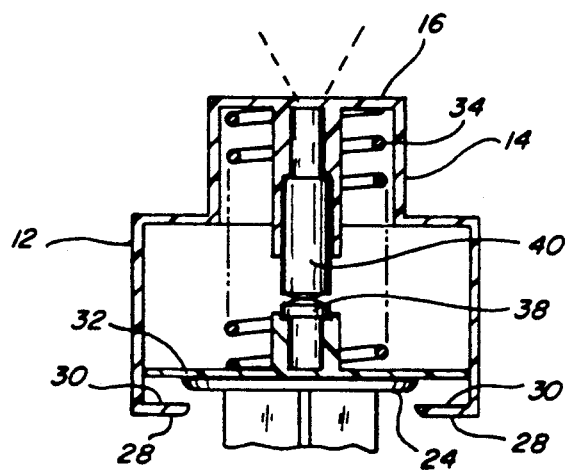
FIG. 3 is a cross-sectional view of the syringe pressure monitoring device of FIG. 1 attached to a plunger portion of a syringe and compressed.

FIGS. 1-3 illustrate one of the preferred embodiments of a syringe pressure monitoring device 10 made in accordance with the present teachings. As best illustrated in FIGS. 2 and 3, the present invention comprises three essential portions; the shell portion 12, the disk portion 32 and the spring member 34, which when assembled form a syringe pressure monitoring device for attachment onto a plunger portion 22 of a syringe 20.

In assembling the present invention, one must first have a tubular shell portion 12 partially closed on each end thereof by a top and a bottom inwardly extending flange, 18 and 28, respectively. Attached to an interior edge 17 of top inwardly extending flange 18 is a tubular upper shell portion 14. The upper edge 15 of tubular upper shell portion 14 is closed by a flat top portion 16. Extending perpendicularly from an interior surface 19 of top portion 16 are extension means 42 to which is secured an indicator source 40. A disk 32 is maintained within an interior portion 29 of shell portion 12 by means of the bottom inwardly extending flange 28. Extending perpendicularly from interior surface 23 of disk 32 are extension means 36 to which is secured a power source 38. Partially compressed between interior surface 19 of top portion 16 and interior surface 23 of disk 32 is a spring 34. Spring 34 is positioned to fit around extension means 42 and 36, indicator source 40 and power source 38. The pressure exerted outwardly by the partially compressed spring 34 forces disk 32 tightly against the interior surface 3 of bottom inwardly extending flange 28.

The pressure monitoring device 10 is installed on a syringe 20 by pushing base member 24 of plunger member 22 of syringe 20 inwardly past bottom inwardly extending flange 28 and positioning base member 24 so as to be held between interior surface 30 of bottom inwardly extending flange 28 and exterior surface 35 of disk 32. The pressure exerted on disk 32 by partially compressed spring 34 also helps hold base member 24 between the disk 32 and bottom inwardly extending flange 28.

When administering an injection to a warm-blooded animal or patient using the pressure monitoring device of embodiment 10, the thumb of the administrator is placed on the top portion 16 of the pressure monitoring device 10 rather than on the base member 24 of plunger member 22 as is done when no pressure monitoring system is used. Other than this one change in thumb positioning, injections are administered in exactly the same manner using the device of the present invention, as used in the past without the device.

As further illustrated in FIG. 3, if during the administration of an injection one were to apply too much force with one's thumb to the top portion 16 of pressure monitoring system 10 (and thus on plunger 22) thus creating a pressure greater than that of the opposing partially compressed spring 34, the spring is forced to further constrict allowing disk 32 to move inwardly into the interior portion 29 of shell portion 12. This inward movement of disk 32 allows indicator source 40 and power source 38 each to come into direct contact with the other. Upon direct contact of indicator source 38 and power source 40, a signal, i.e., a beep sound(s), a light illumination, a color change, or the like indicates that an excess of force has been applied to the plunger 22 and thus excess pressure has been exerted on the fluid(s) within the syringe.

Figure 4:
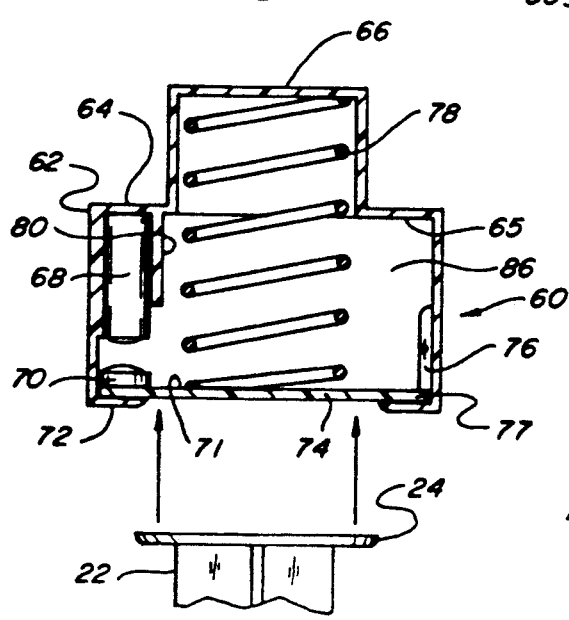
FIG. 4 is a cross-sectional view of another embodiment of the syringe pressure monitoring device of FIG. 1 attached to a plunger portion of a syringe.
Figure 5:
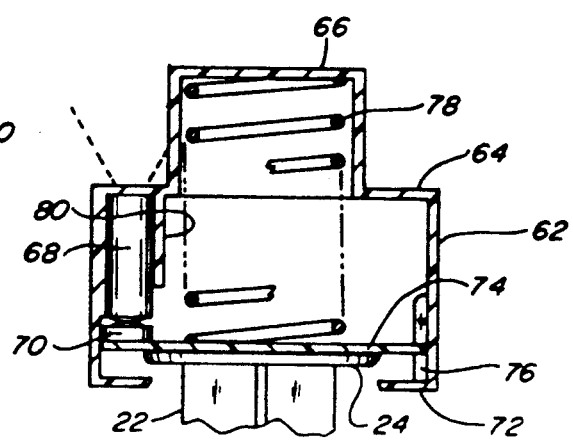
FIG. 5 is a cross-sectional view of the syringe pressure monitoring device of FIG. 4 attached to a plunger portion of a syringe and compressed.

Another embodiment 60 as illustrated in FIGS. 4 and 5 is fairly similar to that of embodiment 10. Differences in embodiment 60 over that of embodiment 10 include extension means 80 which extend perpendicularly from interior surface 65 of top inwardly extending flange 64. An indicator source 68 is secured in position by extension means 80. Power source 70 is likewise secured by means of an adhesive or the like to interior surface 71 of disk member 74 in alignment with indicator source 68. Power source 70 and indicator source 68 are then kept in alignment by means of extending pin member 76 which coincides with a groove 77 formed in disk member 74. Extending pin member 76 and groove 77 work together to prevent the rotational movement of disk member 74.

As best illustrated in FIG. 5, when an excess of force is exerted with one's thumb on top portion 66 of pressure monitoring system 60 (and thus on plunger 84) thus creating a pressure greater than that of the opposing partially compressed spring 78, the spring is forced to further constrict allowing disk member 74 to move inwardly along pin member 76 into the interior portion 86 of shell portion 62. Upon this further constriction of spring member 78 as just described, indicator source 68 and power source 70 each come into direct contact with the other. Upon direct contact of indicator source 68 and power source 70, a signal is initiated to warn the administrator that too much force has been applied on syringe plunger 84.

Another embodiment 100 as illustrated in FIGS. 6 and 7 is again fairly similar to that of embodiment 10. However, in embodiment 100, an outwardly extending flange 116 is attached to a free edge 115 of tubular upper portion 106. Outwardly extending flange 116 is maintained within interior portion 123 of tubular shell portion 102 by means of top inwardly extending flange 114. Disk 125 may be attached by means of an adhesive or the like to interior surface 119 of tubular shell portion 102 and immobile (as illustrated in FIGS. 6 and 7) or maintained within interior portion 123 of tubular shell portion 102 by means of bottom inwardly extending flange 120 and mobile (such as illustrated in FIGS. 2 and 3).

The pressure monitoring system 100 is installed on a syringe 2 in the same manner as pressure monitoring system 10 whereby a base member 24 of a plunger member 22 of syringe 20 is pushed inwardly past bottom inwardly extending flange 120 and positioned to be held between interior surface 121 of bottom inwardly extending flange 120 and exterior surface 127 of either mobile or immobile disk 125.

As best illustrated in FIG. 7, upon administration of an injection to a patient using the pressure monitoring system of embodiment 100, if an excessive force is exerted with one's thumb on to top portion 108 of pressure monitoring system 100 (and thus on plunger 22) creating a pressure greater than that created by the force of opposing partially compressed spring 110, spring 110 is forced to further constrict. As spring 110 further constricts, tubular upper portion 106 slides past inwardly extending flange 114 and into interior portion 123 of tubular shell portion 102. Disk member 125 if mobile also moves into interior portion 123 upon further constriction of spring 110. Upon such constriction of spring member 110 as just described, indicator source 126 and power source 124 each come into direct contact with the other and thus initiate a signal to warn the administrator that too much force has been applied.

Still another embodiment 140 as illustrated in FIGS. 8 and 9 is fairly similar to that of embodiment 10. However, embodiment 140 does not have a disk member similar to disk member 32 of embodiment 10. Rather, spring 148 is attached by means of an adhesive or the like to interior surface 145 of top portion 146. Power source 154 is maintained in position and aligned with indicator source 152 within tubular shell portion 142 by means of flexible flange 156.

The pressure monitoring system 140 is installed on a syringe 20 by pushing base member 24 of plunger member 22 of syringe 20 against extended spring 148 so as to compressed spring 148 and move inwardly past bottom inwardly extending flange 158. Base member 24 is then positioned so as to be held against interior surface 159 of bottom inwardly extending flange 158 by the force of partially compressed spring 148.

As best illustrated in FIG. 9, when administering an injection to a patient, if excessive force is exerted with one's thumb on top portion 146 of pressure monitor 140 (and thus on plunger 22) creating a pressure greater than that created by opposing partially compressed spring 148, the spring is forced to further constrict as base member 24 moves inwardly into interior portion 143 of shell portion 142. Upon further constriction of spring member 148 as just described, base member 24 contacts and bends flexible flange 156 to allow indicator source 152 and power source 154 each to come into direct contact with the other and thus initiating a signal to warn the administrator that too much force has been applied which may have affected the fluids within the syringe.

In constructing each particular embodiment of the pressure monitoring device of the present invention any suitable material natural or synthetic may be used, such as metal, metal alloys, wood, synthetic polymers, synthetic monomers or any suitable and desired combination thereof. The spring portion of the present device is of course constructed from a flexible, resilient natural or synthetic material, such as metal, metal alloys, synthetic polymers, synthetic monomers or any suitable and desired combination thereof. The particular stiffness of the spring portion is pre-determined based on the particular use and characteristic of the pharmaceutical or fluid(s) to be injected so as to have adequate stiffness and resistance to compression. The indicator source may also conceivably be activated by mere contact rather than requiring contact by a power source.

The foregoing has been a description of the preferred embodiments of the present invention. Although many specific details have been described, it should be understood that the description is only for the purpose of explaining the invention, and not limiting it. The scope of the invention may be ascertained from the following appended claims.

What is claimed is:

1. A pressure monitoring device comprising:
   a. a shell portion with means for attachment onto a base portion of a syringe plunger,
   b. a spring within said shell portion, and
   c. an indicator means within said shell portion whereby compression of the spring within the shell portion due to an excessive use of force upon administering an injection to a patient initiates a signal from said indicator means warning an administrator that too much force has been used.

2. The pressure monitoring device of claim 1 wherein said indicator means comprises an indicator source and a power source.

3. The pressure monitoring device of claim 2 wherein said signal is a sound, sounds, color change or light illumination.

* * * * *